US012633002B2

(12) United States Patent
Lee et al.

(10) Patent No.: US 12,633,002 B2
(45) Date of Patent: May 19, 2026

(54) AUGMENTED REALITY IMAGE USING ARTIFICIAL INTELLIGENCE

(71) Applicant: Seoul National University R&DB Foundation, Seoul (KR)

(72) Inventors: Hyuk Jae Lee, Seongnam-si (KR); Tae Ho Lee, Anyang-si (KR); Abesiri Munasinghege Malinga Viduranga, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 169 days.

(21) Appl. No.: 18/374,899

(22) Filed: Sep. 29, 2023

(65) Prior Publication Data

US 2024/0135601 A1    Apr. 25, 2024

(30) Foreign Application Priority Data

Oct. 6, 2022    (KR) ........................ 10-2022-0127898

(51) Int. Cl.
| | |
|---|---|
| *G06T 11/00* | (2006.01) |
| *A61B 90/00* | (2016.01) |
| *G06T 3/40* | (2024.01) |
| *G06T 7/30* | (2017.01) |
| *G06T 7/70* | (2017.01) |

(52) U.S. Cl.
CPC .............. *G06T 11/00* (2013.01); *A61B 90/37* (2016.02); *G06T 3/40* (2013.01); *G06T 7/30* (2017.01); *G06T 7/70* (2017.01); *A61B 2090/365* (2016.02); *A61B 2090/376* (2016.02); *G06T 2207/10081* (2013.01); *G06T 2207/10088* (2013.01); *G06T 2207/10104*
(2013.01); *G06T 2207/10116* (2013.01); *G06T 2207/10132* (2013.01); *G06T 2207/20081* (2013.01); *G06T 2207/20084* (2013.01); *G06T 2207/30196* (2013.01)

(58) Field of Classification Search
None
See application file for complete search history.

(56) References Cited

U.S. PATENT DOCUMENTS

| | | |
|---|---|---|
| 2020/0188028 A1 | 6/2020 | Feiner et al. |
| 2020/0375666 A1 | 12/2020 | Murphy |

FOREIGN PATENT DOCUMENTS

| | | |
|---|---|---|
| KR | 1020210115451 A | 9/2021 |
| KR | 1020220030093 A | 3/2022 |
| KR | 10-2022-0048973 A | 4/2022 |

OTHER PUBLICATIONS

Minar et al. ("CP-VTON+: Clothing Shape and Texture Preserving Image-Based Virtual Try-On"). (Year: 2020).*

(Continued)

*Primary Examiner* — Yanna Wu
(74) *Attorney, Agent, or Firm* — NSIP Law

(57) ABSTRACT

Provided are a method and device for providing a medical augmented reality image using artificial intelligence, and more particularly, provided are a method and device for providing a medical augmented reality image by changing a medical image of a patient captured before an operation according to posture information of the patient during the operation using an artificial intelligence model and matching the changed medical image to a body image of the patient to be output to medical staff during the operation.

6 Claims, 6 Drawing Sheets

Person Representation $p$

X-ray Image          Warped X-ray Image $\hat{c}$          Final result $I_o$

(56)                        References Cited

OTHER PUBLICATIONS

T.H. Lee et al., "GAN-Based Medical Image Registration for Augmented Reality Applications," 2022 IEEE 4th International Conference on Artificial Intelligence Circuits and Systems (AICAS), Incheon, Korea, Jun. 13, 2022, pp. 279-282.
Wang, Bochao, et al. "Toward characteristic-preserving image-based virtual try-on network." *Proceedings of the European conference on computer vision (ECCV)*. 2018.

* cited by examiner

AUGMENTED REALITY IMAGE USING ARTIFICIAL INTELLIGENCE

RELATED APPLICATION(S)

This application claims priority to Korean Patent Application No. 10-2022-0127898, filed Oct. 6, 2022, the entirety of which is incorporated by reference herein.

BACKGROUND OF THE INVENTION

Field of the Invention

The present invention relates to a method, device, and system for providing a medical augmented reality image using artificial intelligence, and more particularly, to a method, device, and system for providing a medical augmented reality image by changing a medical image of a patient captured before an operation according to posture information of the patient during the operation and matching the changed medical image to a body image of the patient to be output to medical staff during the operation using an artificial intelligence model.

Description of the Related Art

Recently, with the development of augmented reality and virtual reality technologies, technologies for augmenting the real world with virtual information have been applied to various fields.

In particular, in the medical field, various image information such as X-ray, CT, and MRI data is being used for operations using AR devices for medical diagnosis and cause analysis of diseases of patients.

In the medical field, medical images such as X-ray, CT, and MRI images are captured to analyze body abnormalities or diseases of patients. For example, medical images may include information on medical abnormalities such as glaucoma, diabetic retinopathy, brain tumor, interstitial lung disease, heart disease, and tuberculosis.

Here, the shape, location, structure, and the like of an affected part in a medical image are used as information serving as criteria for subjective determination of a doctor in the course of treatment.

With the recent development of AR/VR technology, medical image information is used in augmented reality (AR) for medical diagnosis and cause analysis of diseases of patients. However, a marking process is still required to match the shape, location, and structure of a medical image, and the size and characteristics of a marker used in the marking process cause disturbance and inconvenience in surgical environments.

Accordingly, in order to utilize an augmented reality application in surgical environments, there is a need for technology capable of accurately matching the body of a patient and medical image information without using a marker.

CITED REFERENCE

Patent Document (Patent Document 1) Korean Patent Publication No. 10-2022-0030093 (2022 Mar. 10)
(Patent Document 2) Korean Patent Publication No. 10-2021-0115451 (2021 Sep. 27)

SUMMARY OF THE INVENTION

Therefore, the present invention has been made in view of the above problems, and it is an object of the present invention to provide a method, device, and system for providing a medical augmented reality image by changing medical images captured before an operation according to posture information of a patient during the operation and matching the changed medical images with a body image of the patient output to medical staff during the operation using an artificial intelligence model.

Objects of the present invention are not limited to those mentioned above, and other objects not mentioned will be clearly understood by those skilled in the art from the description below.

In accordance with an aspect of the present invention, the above and other objects can be accomplished by the provision of a method of providing a medical augmented reality image using artificial intelligence, the method including obtaining a first medical image of a patient captured before an operation, obtaining a body image of the patient through a medical AR device during the operation, estimating posture information in the body image, obtaining a second medical image by transforming the first medical image according to the estimated posture information on the basis of a first artificial intelligence model, and generating a medical augmented reality image by matching the second medical image to the body image on the basis of a second artificial intelligence model.

In accordance with another aspect of the present invention, there is provided a device for providing a medical augmented reality image using artificial intelligence, the device including a memory configured to store a first artificial intelligence model for obtaining a second medical image by transforming a first medical image of a patient captured before an operation according to posture information during the operation, and a second artificial intelligence model for matching the second medical image to a body image obtained during the operation, a communication unit configured to transmit/receive information to/from an external device, and a processor configured to control the memory and the communication unit, wherein the processor is configured to obtain the first medical image, to obtain a body image through a medical AR device during an operation, to estimate the posture information on the basis of the body image, and to generate a medical augmented reality image to be output to the medical AR device by matching the second medical image to the body image.

In accordance with a further aspect of the present invention, there is provided a system for providing a medical augmented reality image using artificial intelligence, the system including a medical AR device configured to output a real image of a body of a patient and a medical augmented reality image together, an image providing device configured to provide a first training dataset for training a first artificial intelligence model and a second training dataset for training a second artificial intelligence model, the first artificial intelligence model obtaining a second medical image by transforming a first medical image of the patent captured before an operation according to posture information during the operation, the second artificial intelligence model matching the second medical image to a body image captured during the operation, and a medical image matching device configured to obtain a body image through the medical AR device during the operation, to estimate the posture information on the basis of the body image, and to generate a medical augmented reality image to be output to the medical AR device by matching the second medical image to the body image.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Objects and effects of the present invention, and technical configurations for achieving the same will become clear with reference to embodiments which will be described later in detail in conjunction with the accompanying drawings. In describing the present invention, if it is determined that a detailed description of a known function or configuration may unnecessarily obscure the gist of the present invention, the detailed description will be omitted. In addition, the terms described later are terms defined in consideration of the structure, role, and function in the present invention, which may vary according to the intention or practice of a user or an operator.

However, the present invention is not limited to the embodiments disclosed below and may be implemented in a variety of different forms. Only these embodiments are provided to complete the disclosure of the present invention and to fully inform those skilled in the art of the scope of the invention, and the present invention is defined by the claims. Therefore, the definition should be made based on the content throughout this specification.

Throughout the specification, when a certain part "includes" a certain component, it means that it may further include other components without excluding other components unless otherwise stated.

Hereinafter, preferred embodiments of the present invention will be described in more detail with reference to the accompanying drawings.

Figure 1:
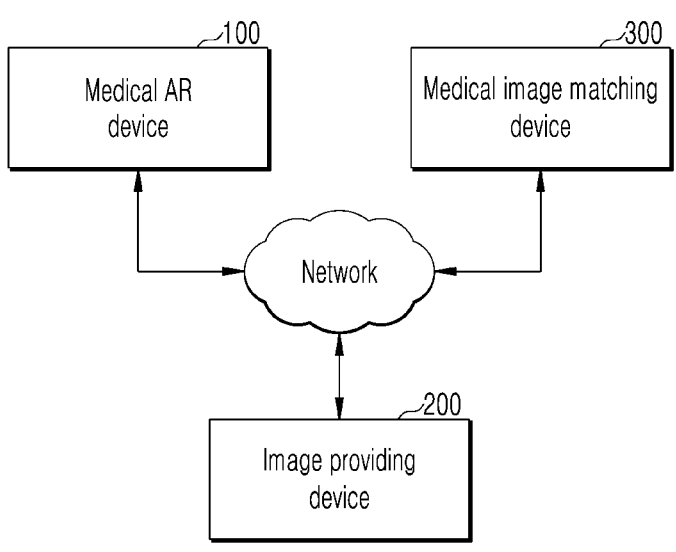
FIG. 1 is a conceptual diagram of a system for providing a medical augmented reality image using artificial intelligence according to an embodiment of the present invention.

FIG. 1 is a conceptual diagram of a system for providing a medical augmented reality image using artificial intelligence according to an embodiment of the present invention.

Referring to FIG. 1, the system for providing a medical augmented reality image using artificial intelligence according to an embodiment may include a medical AR device 100, an image providing device 200, and a medical image matching device 300.

The components shown in FIG. 1 may be connected through a network. This means a connection structure in which information can be exchanged between nodes such as the medical AR device 100, the image providing device 200, and the medical image matching device 300. Examples of such a network include a 3rd Generation Partnership Project (3GPP) network, a Long Term Evolution (LTE) network, a World Interoperability for Microwave Access (WIMAX) network, the Internet, a LAN, a wireless LAN, a WAN, a PAN, a Bluetooth network, a satellite broadcasting network, an analog broadcasting network, a digital multimedia broadcasting (DMB) networks, and the like, but the present invention is not limited thereto.

Prior to description, hereinafter, a medical image captured before an operation is referred to as a first medical image, an image of a body captured by a medical AR device during an operation is referred to as a body image, and an image obtained by transforming the first medical image according to posture information in the body image will be referred to as a second medical image.

First, the medical AR device 100 may provide augmented reality images in a state in which the medical AR device 100 is put on a user such as a doctor or medical staff or not. Augmented reality images provided by the medical AR device 100 include a body image that directly displays only the body of a patient and an affected part information image that displays information about a condition of an affected part of the patient.

The user can view a real image of the patient's body visible through the medical AR device 100 and a medical augmented reality image provided from the medical AR device 100 together.

Specifically, the medical AR device 100 may provide a medical augmented reality image generated by matching a second medical image obtained by transforming a first medical image captured before an operation according to posture information of the patient during the operation to a body image captured during the operation.

Accordingly, the medical staff can view a real image of the affected part of the patient and a medical augmented reality image generated on the basis of a medical image captured by a medical device other than the medical AR device together. Accordingly, the user can check the real image of the affected part of the patient and the augmented reality image based on the medical image captured by another medical device at once and thus need not change their point of gaze to check the medical image captured separately.

Here, the medical image captured by another medical device may be at least one of an X-ray image, a computed tomography (CT) image, a magnetic resonance imaging (MRI) image, a PET image, or an ultrasonic image.

In addition, the medical AR device 100 may include at least one of a head mount display (HMD), a smartphone VR, a HoloLens, mobile glasses, a tablet computer, a laptop, or a PC monitor, but is not limited thereto.

The image providing device 200 may provide a first training data set and a second training data set to the medical image matching device 300.

Specifically, the first training data set may include a medical image, a ground truth image of a transformed medical image (second medical image) when matched, and ground truth labels for a body image to which the second medical image is matched.

For example, the image providing apparatus 200 may store training data sets for vast and various types of body and virtual matched medical images previously disclosed to the public in a database.

Here, a medical image may be at least one of an X-ray image, a computed tomography (CT) image, or a magnetic resonance imaging (MRI) image, which is captured by a medical device other than the medical AR device 100 as described above.

The second training data set may include a second medical image and a mask and body image of the second medical image.

Here, a medical image may be adjusted to the same pixels as pixels corresponding to the image size of an image data set of a virtual try-on network. In addition, a mask of the medical image may be obtained by using a tool (polygon labeling tool) on the medical image.

A method of training an artificial intelligence model using each training data set will be described below.

The image providing device 200 may include a communication module for communicating with the medical AR device 100, a data processor for processing data, and a database storing various types of data.

The medical image matching device 300 may include a separate cloud server or computing device. Although the medical image matching device 300 may be a processor of the medical AR device 100 or a neural network system installed in the image providing device 200, the medical image matching device 300 will be described as a device separate from the medical AR device 100 or the image providing device 200 hereinafter.

Figure 2:
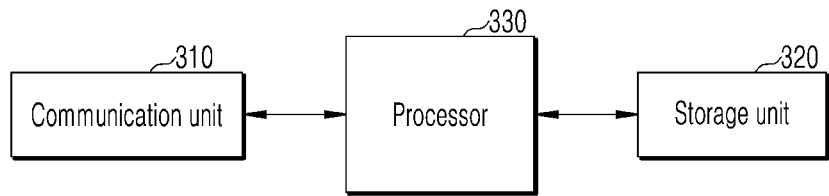
FIG. 2 is a block diagram showing a configuration of a medical image matching device according to an embodiment of the present invention.
Figure 3:
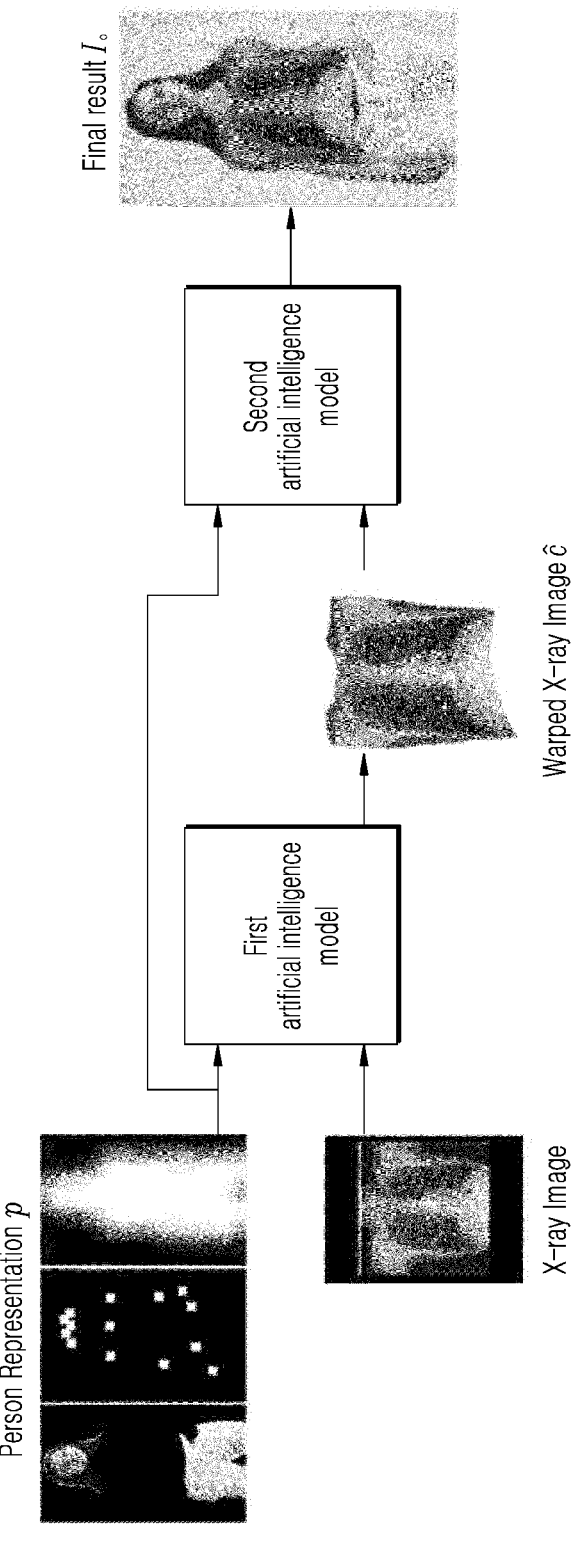
FIG. 3 is a diagram illustrating a structure of a model used in the system for providing a medical augmented reality image using artificial intelligence according to an embodiment of the present invention.

FIG. 2 is a block diagram showing a configuration of the medical image matching device according to an embodiment of the present invention.

Referring to FIG. 2, the medical image matching device 300 may receive a patient's body image and a virtual matching medical image from the medical AR device 100 through a communication unit 320 and receive training data sets from the image providing device 200.

The medical image matching device 300 may construct a medical image virtual matching deep learning model using the training data sets, match a medical image to the patient's body image, and provide a medical augmented reality image. That is, according to the present invention, the medical image can be virtually matched to the patient's body image using a deep learning neural network.

To this end, the medical image matching device 300 may include a memory 310, the communication unit 320, and a processor 330.

The memory 310 may store a first artificial intelligence model for obtaining a second medical image obtained by transforming a first medical image captured before an operation according to posture information during the operation, and a second artificial intelligence model for matching the second medical image to a body image obtained during the operation.

The communication unit 320 may transmit/receive information to/from an external device.

First, the processor 330 acquires a first medical image of a patient captured by a medical device such as MRI, CT, or X-ray equipment instead of the medical AR device 100 before an operation.

In addition, the processor 330 obtains a body image of the patient through a camera of the medical AR device 100 during the operation, estimates posture information in the body image, and acquires a second medical image by transforming the first medical image according to the estimated posture information on the basis of the first artificial intelligence model.

Subsequently, the processor 330 generates a medical augmented reality image by matching the second medical image to the body image on the basis of the second artificial intelligence model.

<Artificial Intelligence Model Training>

Specifically, the processor 330 may first receive the first training data set from the image providing device 200 and train the first artificial intelligence model on the basis of the first training data set.

The first artificial intelligence model may transform a medical image according to posture information of a patient while maintaining the characteristics of the medical image. Here, the first artificial intelligence model may be referred to as a geometric transformation model.

In particular, the first artificial intelligence model may transform a medical image in perspective and then transform the medical image in a detailed step-by-step manner for natural and realistic transformation of the medical image.

In addition, the first artificial intelligence model reflects a loss function during training of a neural network such that features such as lesions, bones, and organs included in a medical image are maintained without being deformed, thereby obtaining results similar to characteristics of a real medical image.

Here, the first artificial intelligence model may be a generative adversarial network (GAN) including a generator network that generates a fake image by combining an image from which a body part has been removed and an arbitrary first medical image, and a discriminator network that discriminates between a fake image and a body image through posture information.

The processor 330 may receive a first medical image and a body image on the basis of a GAN, process the image by removing a body part from the body image, extract posture information of the body image, and preprocess the posture information such that it will be used for learning.

As described above, the first medical image may be at least one of an X-ray image, a computed tomography (CT) image, or a magnetic resonance imaging (MRI) image of the patient captured before an operation, and the body image may be acquired through the medical AR device 100 during the operation.

Specifically, a generator of the GAN generates a fake image through a latent vector, and a discriminator determines whether or not the fake image is real on the basis of a real body image and the fake image obtained by combining a body image from which a body part has been removed with the first medical image. Then, a loss is calculated on the basis of the determined probability, the generator is trained to generate a fake image more similar to a real image through gradient descent, and the discriminator is trained to classify a real image.

In this way, the first artificial intelligence model can process a medical image captured before an operation such that the medical image becomes almost identical to a body image of a patient during the operation to almost exactly match the patient's body with the medical image.

Further, the processor 330 may receive the second training data set from the image providing device 200 and train the second artificial intelligence model on the basis of the second training data set.

Figure 4:
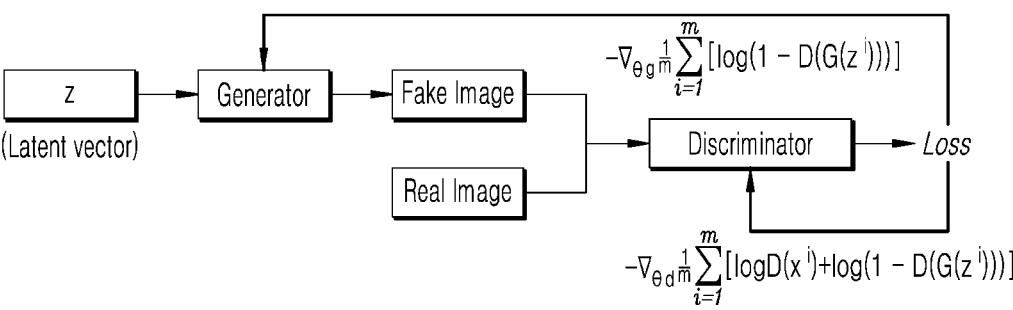
FIG. 4 is a diagram illustrating a structure of a second artificial intelligence model according to an embodiment of the present invention.

Here, the second artificial intelligence model may be a model obtained by training a try-on model (TOM) of a virtual try-on network shown in FIG. 4 through transfer learning using the second training data set. Here, TOM is a pipeline for composition of a final virtual fitting image of the original virtual try-on network.

Figure 5:
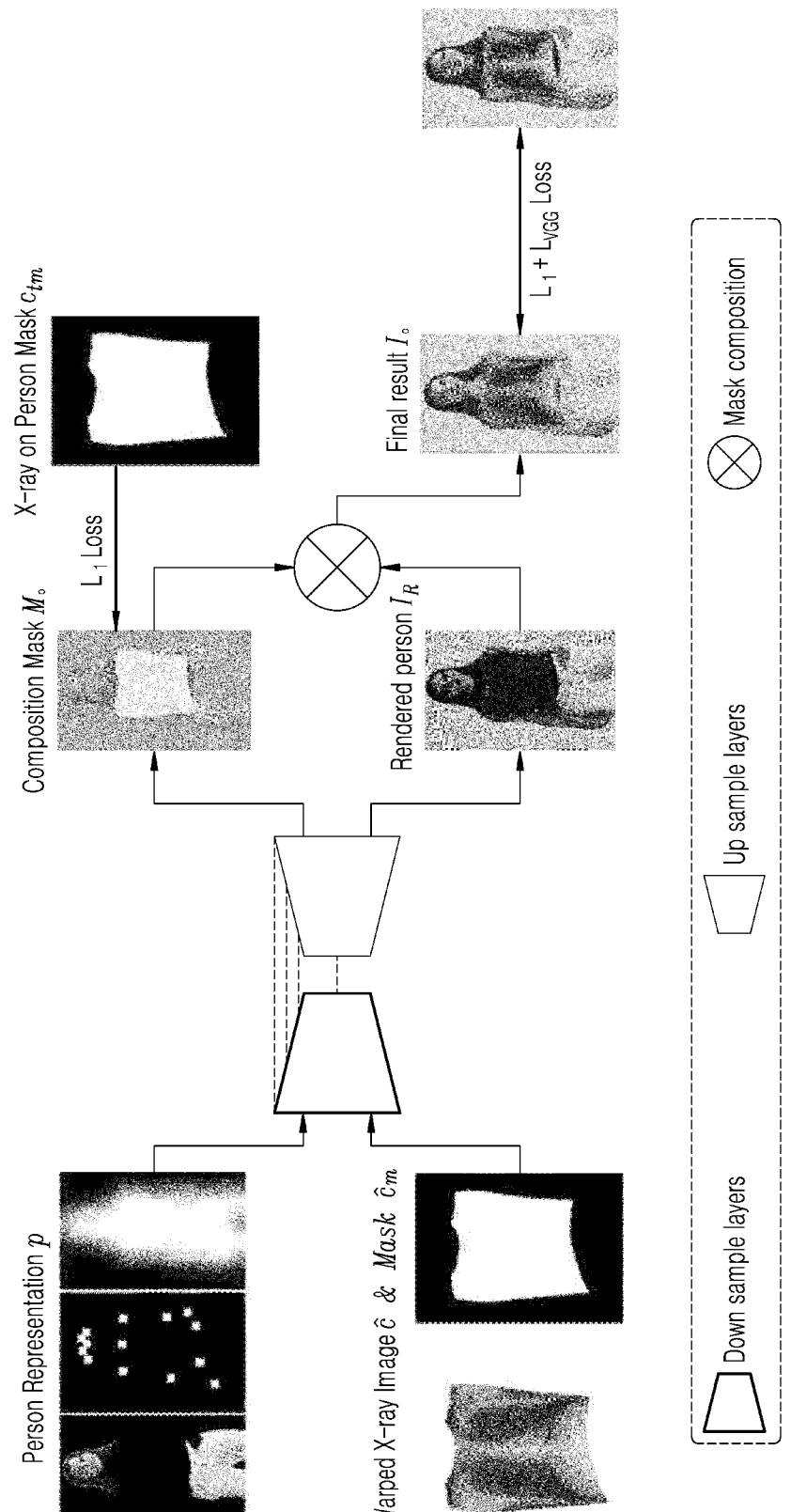
FIG. 5 is a diagram illustrating a structure of a supervised-trained try-on model (TOM) according to an embodiment of the present invention.

In one embodiment of the present invention, as shown in FIG. 5, the TOM receives a posture information image through segmentation from a patient's body image and a warped medical image (warped X-ray image ĉ, second medical image) as inputs, and obtains a rendered image from the warped medical image ĉ using a composition mask $M_O$ to generate a final result $I_O$.

In the virtual try-on network, a body shape component can be obtained through a human parser. In order to obtain posture information from results of the human parser, downsampling to a lower resolution may be performed. Since this technology is known technology, detailed descriptions thereof will be omitted.

The TOM renders a body image (rendered person $I_R$) using U-Net (six 2-stride downsampling convolutional layers and six upsampling layers) and predicts the composition mask $M_O$.

The U-Net modifies and extends a full convolutional network for more precise segmentation, and designs a skip connection between downsampling and upsampling paths that provide local information to global information during upsampling.

Then, the TOM composites the rendered person image $I_R$ and the warped medical image ĉ (second medical image) using the composition mask $M_O$.

The loss function of TOM is as follows.

$$\mathcal{L}_{total} = \mathcal{L}_{perc}(I_f,I_t)+\|I_f-I_t\|_1+\|M-M_c\|_1$$

Here, the first term is a VGG perceptual loss, the second term is a per-pixel L1 loss between $I_f$ and $I_t$, the third term is a per-pixel L1 loss between the composition mask and a cloth mask, and $$\mathcal{L}_{perc}(I_f, I_t) = \sum_{i=5}^{5} \|\Theta_1(I_f) - \theta_1(I_t)\|_1$$

where $\theta i(I)$ indicates a feature map of an image I of an i-th layer in a visual recognition network $\theta$ using VGG19 (K. Simonyan and A. Zisserman, "Very Deep Convolutional Networks for Large-scale Image Recognition," arXiv Preprint arXiv: 1409.1556, 2014) pretrained on ImageNet.

<Generation of Medical Augmented Reality Image>

The processor 330 estimates posture information in a body image acquired through the medical AR device 100 during an operation, and transforms the first medical image (medical image obtained before the operation) according to the estimated posture information on the basis of the trained first artificial intelligence model to obtain the second medical image.

Subsequently, the processor 330 matches the second medical image to the body image on the basis of the second artificial intelligence model and outputs a medical augmented reality image through the medical AR device 100.

Accordingly, the medical AR device 100 can simultaneously output a real body image of a patient that can be viewed during an operation and an augmented reality image based on a medical image captured before the operation.

Figure 7:
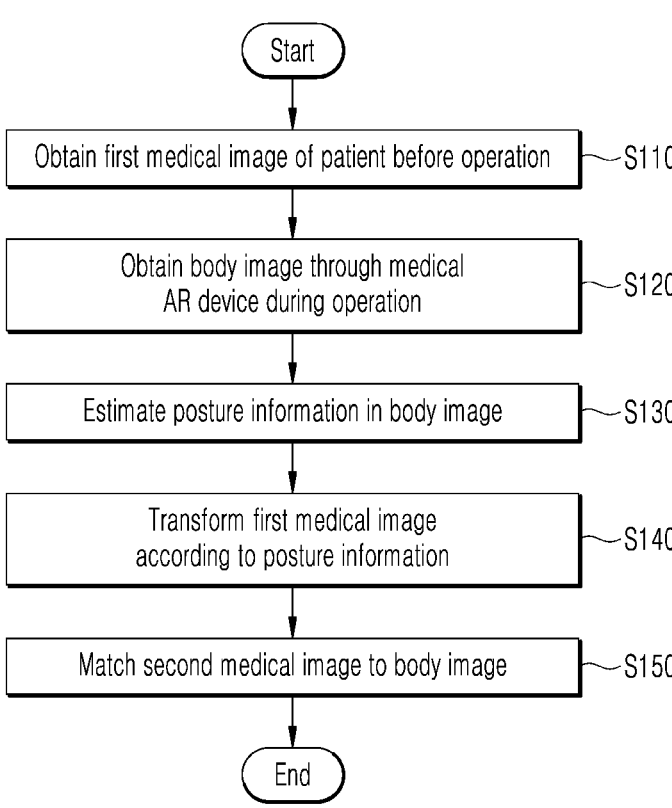
FIG. 7 is a flowchart illustrating a method of providing a medical augmented reality image using artificial intelligence according to an embodiment of the present invention.

FIG. 7 is a flowchart illustrating a method of providing a medical augmented reality image using artificial intelligence according to an embodiment of the present invention. The method may be performed in substantially the same configuration as the system for providing a medical augmented reality image using artificial intelligence shown in FIG. 1. Therefore, the same components as those of the system for providing a medical augmented reality image using artificial intelligence shown in FIG. 1 are denoted by the same reference numerals, and redundant description will be omitted.

In addition, the method of providing a medical augmented reality image using artificial intelligence according to the present embodiment may be executed by software (application) using machine learning.

First, a first medical image of a patient may be obtained before an operation (S110).

Here, the first medical image may be at least one of an X-ray image, a computed tomography (CT) image, or a magnetic resonance imaging (MRI) image.

Next, a body image of the patient may be obtained through a medical AR device during the operation (S120).

Here, the medical AR device may include at least one of a head-mounted display (HMD), a smartphone VR, a HoloLens, or mobile glasses, but is not limited thereto. Here, in preparation for using a virtual try-on network model in the future, the size of the body image obtained through the medical AR device may be adjusted to the size of an image of a target person input to the virtual try-on network model.

Next, posture information in the body image may be estimated (S130). To this end, a human parser model may be used.

Next, a second medical image may be obtained by transforming the first medical image according to the estimated posture information on the basis of a first artificial intelligence model (S140).

Here, the first artificial intelligence model may transform a medical image according to the posture information of the patient while maintaining the characteristics of the medical image. In particular, the first artificial intelligence model may transform the medical image in perspective and then transform the medical image in a detailed step-by-step manner for natural and realistic transformation of the medical image.

In addition, the first artificial intelligence model reflects a loss function during training of a neural network such that features such as lesions, bones, and organs included in a medical image are maintained without being deformed, thereby obtaining results similar to characteristics of a real medical image.

In one embodiment, the first artificial intelligence model may be a generative adversarial network (GAN) including a generator network that generates a fake image by combining an image from which a body part has been removed and an arbitrary first medical image, and a discriminator network that discriminates between a fake image and a body image through posture information.

A warped medical image (second medical image) may be obtained according to the posture information of the patient through the aforementioned GAN.

Subsequently, a medical augmented reality image may be generated by matching the second medical image to the body image on the basis of a second artificial intelligence model (S150).

The second artificial intelligence model may be a model obtained by training a try-on model (TOM) of the virtual try-on network shown in FIG. 4 through transfer learning using the second training data set. Here, the TOM is a pipeline for composition of a final virtual fitting image of the original virtual try-on network.

In one embodiment of the present invention, as shown in FIG. 5, the TOM receives a posture information image through segmentation from a patient's body image and a warped medical image (warped X-ray image ĉ, second medical image) as inputs and obtains a rendered image from the warped medical image ĉ using a composition mask $M_O$ to generate a final result $I_O$.

In the virtual try-on network, a body shape component can be obtained through a human parser. In order to obtain posture information from results of the human parser, down-sampling to a lower resolution may be performed. Since this technology is known technology, detailed descriptions thereof will be omitted.

The TOM renders a body image (rendered person $I_R$) using U-Net (six 2-stride downsampling convolutional layers and six upsampling layers) and predicts the composition mask $M_O$.

The U-Net modifies and extends a full convolutional network for more precise segmentation, and designs a skip connection between downsampling and upsampling paths that provide local information to global information during upsampling.

Then, the TOM composites the rendered person image $I_R$ and the warped medical image ĉ (second medical image) using the composition mask $M_O$.

In this way, the medical augmented reality image generated on the basis of matching of the second medical image to the body image may be output to the medical AR device.

The above-described system for providing a medical augmented reality image may be implemented by a computing device including at least some of a processor, a memory, a user input device, and a presentation device. The memory is a medium that stores computer-readable software, applications, program modules, routines, instructions, and/or data coded to perform a specific task when executed by the processor. The processor may read and execute computer-readable software, applications, program modules, routines, instructions, and/or data stored in the memory.

The user input device may be a means for allowing a user to input a command to execute a specific task to the processor or input data necessary to execute a specific task. The user input device may include a physical or virtual keyboard or keypad, key buttons, a mouse, a joystick, a trackball, a touch-sensitive input means, a microphone, or the like. The presentation device may include a display, a printer, a speaker, a vibrator, or the like.

The computing device may include a variety of devices such as smartphones, tablets, laptop computers, desktop computers, servers, and clients. The computing device may be a single stand-alone device or may include multiple computing devices operating in a distributed environment including multiple computing devices cooperating with each other over a communications network.

In addition, the above-described method of providing a medical augmented reality image may be executed by a computer device including a processor and a memory storing computer readable software, applications, program modules, routines, instructions, and/or data structures coded to execute a method of providing a medical augmented reality image using an agent model when executed by the processor.

The present embodiments described above may be implemented through various means. For example, the present embodiments may be implemented by hardware, firmware, software, or a combination thereof.

In the case of hardware implementation, the method of providing a medical augmented reality image using artificial intelligence according to the present embodiments may be implemented by one or more application specific integrated circuits (ASICs), digital signal processors (DSPs), digital signal processing devices (DSPDs), programmable logic devices (PLDs), field programmable gate arrays (FPGAs), processors, controllers, microcontrollers, or microprocessors.

For example, the method of providing a medical augmented reality image according to embodiments may be implemented using a machine learning semiconductor device in which neurons and synapses of a deep neural network are implemented as semiconductor elements. In this case, the semiconductor elements may be currently used semiconductor elements such as SRAMs, DRAMs, NANDs, and the like, next-generation semiconductor elements, RRAMs, STT MRAMs, PRAMs, or the like, or a combination thereof.

In a case in which the method of providing a medical augmented reality image according to the embodiments is implemented using a machine learning semiconductor device, results (weights) of training an agent model with software may be transferred to synaptic mimic elements arranged in an array or training may be performed in a machine learning semiconductor device.

In the case of implementation by firmware or software, the method of providing a medical augmented reality image according to the present embodiments may be implemented in the form of a device, a procedure, or a function that performs the functions or operations described above. Software code may be stored in a memory unit and driven by a processor. The memory unit may be located inside or outside the processor and exchange data with the processor through various means known in the art.

Further, the terms "system," "processor," "controller," "component," "module," "interface," "model," and "unit" described above generally refer to computer-related entity hardware, a combination of hardware and software, software or software that is being executed. For example, the above-described components may be a process driven by a processor, a processor, a controller, a control processor, an entity, an execution thread, a program, and/or a computer, without being limited thereto. For example, both an application being executed in a controller or a processor and the controller or the processor may be components. One or more components may reside within a process and/or an execution thread, and components may be present in one device (e.g., system, computing device, or the like) or may be distributed across two or more devices.

Another embodiment provides a computer program stored in a computer recording medium to perform the above-described method of providing a medical augmented reality image. In addition, another embodiment provides a computer-readable recording medium on which a program for realizing the above-described method of providing a medical augmented reality image is recorded.

The program recorded on a recording medium may be read, installed, and executed in a computer to execute the above-described steps. In this way, in order for the computer to read the program recorded on the recording medium and execute the functions implemented by the program, the above-described program may include code encoded in a computer language such as C, C++, JAVA, Python, R, C #, or a machine language that can be read by a processor (CPU) of a computer through a device interface of the computer.

This code may include functional code related to functions defining the above-described functions, and may include control code related to an execution procedure necessary for the processor of the computer to execute the above-described functions according to a predetermined procedure.

In addition, such code may further include memory reference related code representing a location (address number) of an internal or external memory of a computer, at which additional information or media necessary for the processor of the computer to execute the above-mentioned functions should be referred to.

In addition, in a case in which the processor of the computer needs to communicate with any other remote computer or server in order to execute the above-mentioned functions, the code may further include communication-related code with respect to how the processor of the computer communicates with any other remote computer or server using a communication module of the computer, what kind of information of media should be transmitted and received during communication, and the like.

A computer-readable recording medium on which the above-described program is recorded includes, for example, a ROM, a RAM, a CD-ROM, a magnetic tape, a floppy disk, an optical media storage device, and the like.

Further, the computer-readable recording medium is distributed to computer systems connected through a network, and thus computer-readable code can be stored and executed in a distributed manner.

In addition, a functional program for implementing the present invention, code and code segments related thereto, and the like may be easily inferred or changed by programmers skilled in the art in consideration of a system environment of a computer that reads a recording medium and executes a program.

Figure 6:
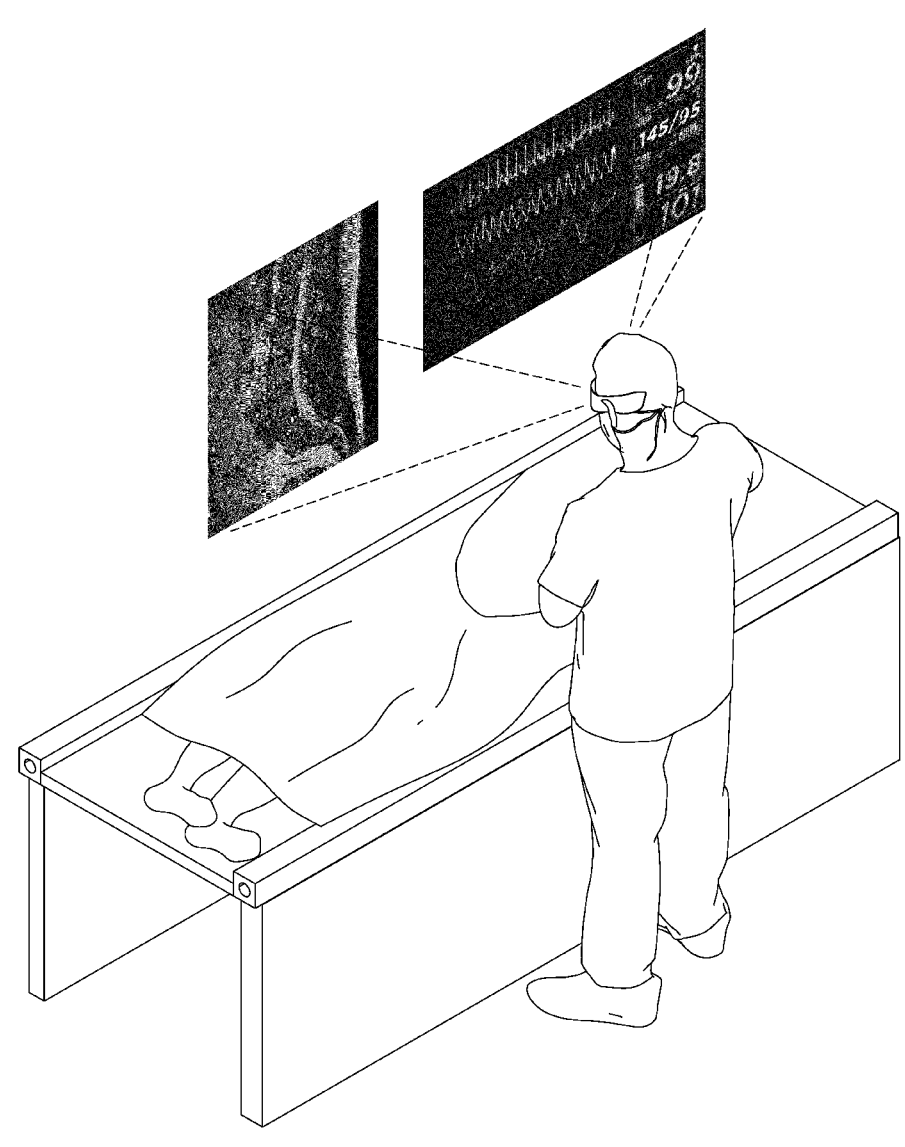
FIG. 6 is a diagram showing an example of a medical AR device according to an embodiment of the present invention.

The method of providing a medical augmented reality image described with reference to FIG. 6 may also be implemented in the form of a recording medium including instructions executable by a computer such as an application or a program module executed by the computer. Computer readable media may be any available media that can be accessed by a computer and include volatile and nonvolatile media, removable and non-removable media. Further, computer readable media may include all computer storage media. Computer storage media include volatile and non-volatile, removable and non-removable media implemented in any method or technology for storage of information such as computer readable instructions, data structures, program modules or other data.

The above-described method of providing a medical augmented reality image may be executed by a default application (which may include a program included in a default platform, operating system, or the like installed in a terminal) installed in the terminal, or may be executed by an application (that is, a program) directly installed by a user in a master terminal through an application providing server such as an application store server and a web server related to the application or the corresponding service.

Accordingly, the above-described method of providing a medical augmented reality image may be implemented as an application (that is, a program) installed in a terminal by default or directly installed by a user and may be recorded on a computer-readable recording medium of a terminal.

According to the method, device, and system for providing medical augmented reality images using artificial intelligence according to an embodiment of the present invention, it is possible to correctly match the body of a patient and medical image information without using markers in order to utilize an augmented reality application in a surgical environment.

In addition, according to the present invention, by providing medical images captured before an operation to medical staff during the operation using augmented reality technology, the medical staff can recognize images of an affected part or information images about the affected part together with the actual affected part of a patient without continuously checking a separate output screen during the operation.

The effects of the present invention are not limited to those mentioned above, and other effects not mentioned will be clearly understood by those skilled in the art from the description below.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

Therefore, the embodiments described above are provided to completely inform those skilled in the art of the scope of the invention, and thus the embodiments should be understood that they are illustrative in all respects and not limiting, and the present invention is only defined by the scope of the claims.

What is claimed is:

1. A method of providing a medical augmented reality image using artificial intelligence, the method comprising:
   obtaining a first medical image of a patient captured before an operation;
   obtaining a body image of the patient through a medical AR device during the operation;
   estimating posture information in the body image;
   obtaining a second medical image by transforming the first medical image according to the estimated posture information on the basis of a first artificial intelligence model; and
   generating a medical augmented reality image by matching the second medical image to the body image on the basis of a second artificial intelligence model.

2. The method of claim 1, further comprising outputting the medical augmented reality image to the medical AR device.

3. The method of claim 1, wherein the obtaining a first medical image comprises obtaining the first medical image on the basis of one of an X-ray image, a computed tomography (CT) image, a magnetic resonance imaging (MRI) image, a PET image, and an ultrasonic image.

4. The method of claim 1, further comprising training the second artificial intelligence model with a medical image as an input using a first training data set in which images obtained by matching medical images to persons are labeled.

5. The method of claim 1, further comprising training a try-on model (TOM) of a virtual try-on network as the second artificial intelligence model through transfer learning,
   wherein the TOM is trained using a second training data set including the second medical image, a mask of the second medical image, and a body image.

6. The method of claim 5, wherein obtaining the second training data set on the basis of the X-ray image and a body image to which the X-ray image has been matched comprises:
   adjusting the X-ray image to the same pixels as pixels corresponding to an image size of an image data set of the virtual try-on network; and obtaining a mask of the X-ray image using a polygon
labeling tool for the adjusted X-ray image.

* * * * *